(12) United States Patent
de la Guardia et al.

(10) Patent No.: US 7,874,299 B2
(45) Date of Patent: Jan. 25, 2011

(54) METHODS OF NEUTRALIZING RELAXED HAIR AND COMPOSITIONS FOR SAME

(75) Inventors: Mario M. de la Guardia, Woodstock, GA (US); Tony Ray Adair, Daphne, AL (US)

(73) Assignee: Strength of Nature, LLC, Atlanta, GA (US)

( * ) Notice: Subject to any disclaimer, the term of this patent is extended or adjusted under 35 U.S.C. 154(b) by 1184 days.

(21) Appl. No.: 10/654,233

(22) Filed: Sep. 2, 2003

(65) Prior Publication Data

US 2005/0048004 A1 Mar. 3, 2005

(51) Int. Cl.
*A45D 7/04* (2006.01)
*A61Q 5/04* (2006.01)

(52) U.S. Cl. ............... 132/205; 132/204; 424/70.2; 424/70.1

(58) Field of Classification Search ............... None
See application file for complete search history.

(56) References Cited

U.S. PATENT DOCUMENTS

| | | | |
|---|---|---|---|
| 3,368,941 A | 2/1968 | Boosen et al. | |
| 3,396,736 A | 8/1968 | Shansky et al. | |
| 3,399,682 A | 9/1968 | Isaji et al. | |
| 4,630,621 A | 12/1986 | Pontani | 132/7 |
| 4,776,856 A | 10/1988 | Tennigkeit et al. | 8/406 |
| 4,871,530 A * | 10/1989 | Grollier et al. | 424/47 |
| 4,992,077 A | 2/1991 | Tennigkeit et al. | 8/406 |
| 5,006,127 A | 4/1991 | Tennigkeit et al. | 8/406 |
| 5,094,662 A | 3/1992 | Schultz et al. | 8/405 |
| 5,161,553 A | 11/1992 | Cohen et al. | 132/205 |
| 5,188,639 A | 2/1993 | Schultz et al. | 8/405 |
| 5,340,367 A | 8/1994 | Schultz et al. | 8/432 |
| 5,635,168 A | 6/1997 | Burns et al. | |
| 5,988,180 A | 11/1999 | Bergstrom | 132/204 |
| 6,173,717 B1 | 1/2001 | Schonert et al. | 132/202 |
| 6,231,844 B1 * | 5/2001 | Nambu | 424/70.31 |
| 6,562,327 B1 | 5/2003 | Nguyen et al. | |

FOREIGN PATENT DOCUMENTS

| | | | |
|---|---|---|---|
| EP | 0260716 | | 9/1987 |
| EP | 0352375 | | 7/1988 |
| EP | 0328816 | | 11/1988 |
| WO | WO 93/00882 | * | 1/1993 |
| WO | WO 9609030 | | 3/1996 |

OTHER PUBLICATIONS

U.S Appl. No. 10/959,758, dated Jul. 13, 2010, Request for Continued Examination (RCE) Filed.
U.S Appl. No. 10/959,758, dated May 13, 2010, Notice of Appeal Filed.
U.S Appl. No. 10/959,758, dated Nov. 9, 2009, Final Rejection.
U.S Appl. No. 10/959,758, dated Aug. 5, 2009, Response to Non-Final Office Action.
U.S Appl. No. 10/959,758, dated Feb. 5, 2009, Non-Final Office Action.
U.S Appl. No. 10/959,758, dated Dec. 17, 2008, Response to Restriction Requirement.
U.S Appl. No. 10/959,758, dated Jun. 17, 2008, Restriction Requirement.
Application No. 2004/7004, dated Jul. 27, 2005, Letters Patent.

* cited by examiner

*Primary Examiner*—Jyothsna A Venkat
(74) *Attorney, Agent, or Firm*—Ballard Spahr LLP (57) ABSTRACT

The present invention relates to processes for neutralizing relaxed hair. Still further, the present invention relates to neutralizer compositions for use on relaxed hair. Still further, the present invention relates to a system for neutralizing relaxed hair. Yet further, the invention relates to relaxed hair neutralized by the compositions and methods disclosed herein.

12 Claims, 1 Drawing Sheet

Figure 1

All heads relaxed on one side with Profectiv Relaxer (Strength of Nature, Savannah, GA) and neutralizing mousse composition ("P")

Other side of each head treated with commercial no-lye relaxer and neutralizing shampoo as-supplied and according to manufacturer's directions (A=Dark & Lovely; B=Optimum; C=Soft & Beautiful; D= Precise)

METHODS OF NEUTRALIZING RELAXED HAIR AND COMPOSITIONS FOR SAME

FIELD OF THE INVENTION

The present invention relates to processes for neutralizing relaxed hair. Still further, the present invention relates to neutralizer compositions for use on relaxed hair. Still further, the present invention relates to a system for neutralizing relaxed hair. Yet further, the invention relates to relaxed hair neutralized by the compositions and methods disclosed herein.

BACKGROUND OF THE INVENTION

Hair is an exceedingly strong fiber. This strength is conferred primarily by disulfide bonds within the cortex of the hair fiber and by a protective cuticle layer that encapsulates the entire hair fiber. The natural degree of curliness of one's hair is largely determined by the orientation of these disulfide bonds. In order to change the physical configuration of hair, these disulfide bonds must be broken. When hair is exceedingly curly in its natural state, fairly aggressive conditions must normally be used to substantially lessen or eliminate the amount of curl. Simply put, the curlier the hair, the more curl that needs to be removed to make the hair straight and, in turn, the more disulfide bonds need to be broken to make the hair straight.

In order to straighten exceedingly curly hair, alkaline compositions must be used. These compositions differ from the thiol-based compositions used in perming in that bond breakage is achieved by hydroxide-containing compounds. Hydroxides are very strong reducing agents and the compositions in which they are formulated are highly alkaline. Accordingly, the pH of relaxer compositions is generally within the range of pH 12 to pH 14. In most circumstances, compositions for the straightening of exceedingly curly hair are termed "lye" type and "no-lye" type compositions. The relaxing process is usually combined with mechanical straightening of the hair, such as by combing, where straightening occurs through changing of the relative positions of opposite polypeptide chains.

As would be understood by one of ordinary skill in the art, under strongly alkaline conditions, such as those conferred by the application of typical relaxer compositions to hair, the disulfide bonds of cystine in hair are converted to stable, irreversible crosslinks of primarily lanthionine with some lysinoalanine. Thus, unlike when hair is reduced with thiol or bisulfite relaxers, a chemical oxidative re-linking step is unnecessary. Rather, the only step required following an alkaline relaxer is to promptly remove the relaxing composition by rinsing the hair with water, and to substantially neutralize all remaining alkaline material to avoid damage to the hair protein or skin. For this purpose, a neutral pH or acidic pH shampoo is applied to the hair to neutralize and remove residual alkaline material from the hair and scalp.

In use, after rinsing the hair of most of the excess relaxer composition, the shampoo neutralizer is applied to the hair. In order to make sure that substantially all of the alkalinity is removed from the hair, care must be taken to fully distribute the shampoo neutralizer through the hair. As such, existing methods of neutralizing relaxed hair invariably require the neutralizer shampoo composition to be massaged or kneaded into the relaxed hair.

However, when hair is in its relaxed state i.e., after straightening but before the alkalinity is removed, the fibers are easily stretched, twisted, or broken. Those skilled in the art will recognize that the studies given in the current literature clearly demonstrate that chemical treatments such as bleaching, waving, and straightening cause changes in the physical properties of hair and related fibers. Measurements of parameters such as Young's Modulus, Load-Elongation Curves and the like have shown that: (1) wet hair stretches more easily than dry hair; (2) chemically treated hair loses some of its tensile strength; (3) the amount of force required to stretch a wet chemically treated hair is lower than that required to stretch a wet, non-treated hair to the same extent; and (4) the amount of total force required to reach the breaking point in a wet, chemically treated hair is lower than that required to reach the point of breakage in wet, non-treated hair. Excessive stretching can also result in cuticle lifting and fiber splitting.

The elliptical shape of hair fibers of people of African descent, so-called "kinky" or "curly" hair is also well documented in the literature. Hair of this type tends to have a combination of areas of fairly normal cross-sectional area with intermittent bends and twists where the cross-sectional area of the hair fiber is reduced or narrowed. These areas of reduced cross-sectional area in effect create natural weak spots where mechanical forces applied to the hair are concentrated over a smaller area. Thus, persons with this type of hair are inherently more at risk of hair damage by mechanical forces applied to the hair fiber than are persons with hair of more uniform cross-sectional area. Further, excessive stretching and twisting can result in damage to or loss of hair's protective cuticle leaving the hair vulnerable to damage from heat styling, combing, and environmental effects of natural weathering. Accordingly, when a shampoo neutralizer is massaged or kneaded into the relaxed hair, hair breakage necessarily results because of the application of force to the relaxed hair from the massaging or kneading of the neutralizer shampoo into the hair. Such breakage, which may be considerable, normally occurs even when the operator is exercising care in applying the shampoo neutralizer to the relaxed hair.

In light of the above, it would be desirable to have a process for neutralizing relaxed hair that minimizes or substantially eliminates the chance of hair damage during neutralization. Further, it would be desirable to have a process where effective neutralization of reduced hair is conferred without having to substantially manipulate the hair to apply the neutralizer composition. Still further, it would be desirable to have hair that is less damaged after relaxing and neutralizing hair.

SUMMARY OF THE INVENTION

The present invention relates to processes for use with "lye" or "no-lye" relaxers. Still further, the present invention relates to neutralizer mousse compositions for use on relaxed hair. Still further, the present invention relates to a system for neutralizing relaxed hair. Yet further, the invention relates to relaxed hair neutralized by the compositions and methods disclosed herein. Hair neutralized according to the methods and compositions herein exhibits at least about 10% less breakage than hair neutralized using shampoo neutralizers.

Additional advantages of the invention will be set forth in part in the description that follows, and in part will be apparent from the description, or can be learned by practice of the invention. The advantages of the invention will be realized and attained by means of the elements and combination particularly pointed out in the appended claims. It is to be understood that both the foregoing general description and the

DETAILED DESCRIPTION OF THE INVENTION

Figure 1:
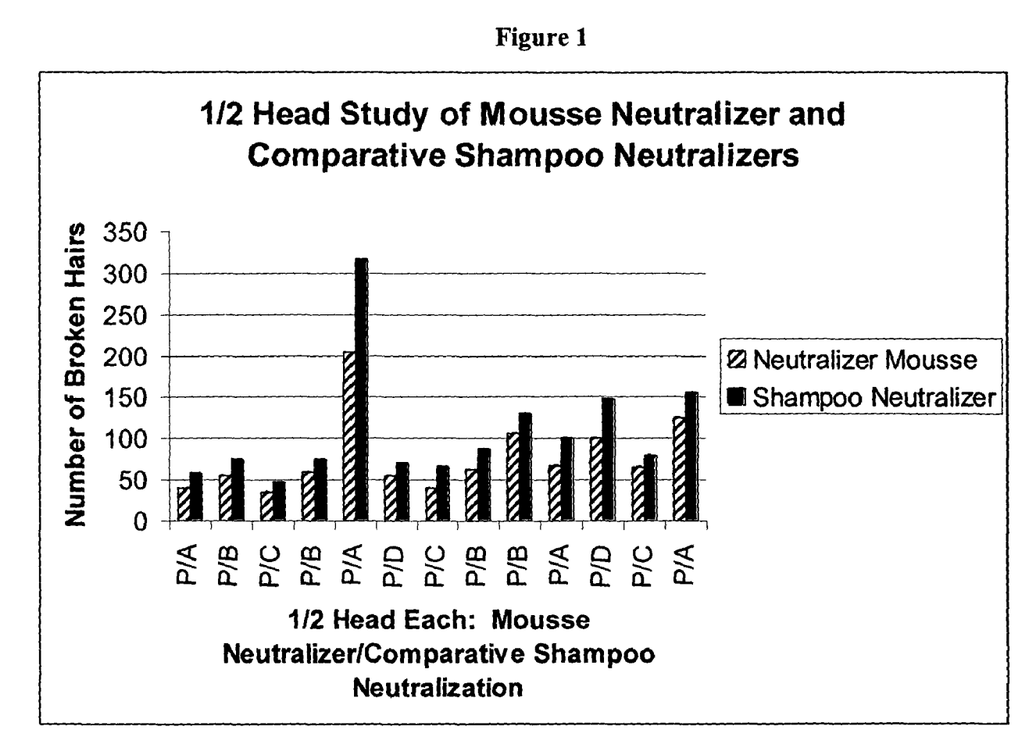
FIG. 1 is a graph of a comparison of hair damage with the neutralizer mousse compositions of the invention and comparative shampoo-type neutralizers.

The present invention can be understood more readily by reference to the following detailed description of the invention and the Examples included herein and to the FIGURE and its previous and following description. It is also to be understood that the terminology used herein is for the purpose of describing particular aspects only and is not intended to be limiting.

It must be noted that, as used in the specification and the appended claims, the singular forms "a," "an" and "the" include plural referents unless the context clearly dictates otherwise. Thus, for example, reference to "an acid" includes mixtures of acids. Often ranges are expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

In the specification and in the claims that follow, reference will be made to a number of terms that shall be defined to have the following meanings:

The term "exceedingly curly hair" denotes hair that naturally exhibits a tight curl or wave pattern and will be referred to herein generally as "hair." Such hair may also be known to one of ordinary skill in the art as "kinky hair," "ethnic hair" or "curly" hair.

The term "hair relaxing" as used herein refers to a treatment whereby hair is treated under a highly-alkaline pH of about greater than about pH 12 to about pH 14, wherein the composition used to relax the hair comprises a water-soluble chemical base. The composition used to relax hair is referred to herein as the "relaxing agent" or "relaxer." The compositions suitable for use herein can be "lye" and "no-lye" relaxing agents, as such materials would be known to one of ordinary skill in the art. Such compositions are discussed in detail in U.S. Pat. No. 6,562,327, the disclosure of which is incorporated herein in its entirety by this reference for its discussion of relaxing agents.

In particular, relaxing agents suitable for use herein can comprise one or more of: an alkali metal hydroxide, such as sodium hydroxide, potassium hydroxide, or lithium hydroxide; alkali earth metal hydroxide, such as calcium hydroxide, barium hydroxide and strontium hydroxide or oxides thereof capable of forming hydroxides in water; or a relatively strong organic base, such as guanidine, guanidine hydroxide or quaternary ammonium hydroxide. Yet still further, the relaxing agents can comprise liquid or cream (emulsified) compositions or a combination thereof.

"Relaxed hair" means hair that has been treated with the relaxing agent. As used herein, "relaxed hair" is hair that has not yet been neutralized.

The term "neutralize" is used herein to generally denote a post-relaxer treatment whereby residual alkalinity is eliminated from relaxed hair. A neutralizer is applied substantially immediately to the relaxed hair following completion of the relaxing step, typically after the relaxing agent has been completely removed or almost completely removed from the relaxed hair by one or more rinsing steps. "Relaxed and neutralized hair" is hair that has been subjected to hair relaxing, followed by neutralization as described further herein.

The term "mousse," as used herein, is equivalent to foam, and refers to the dispensed product, unless otherwise specified. The neutralizer mousse compositions of the present invention are packaged in appropriate containers equipped with the appropriate dispensers and in an appropriate manner so as to provide a product which dispenses a mousse product, the containers, dispensers and necessary techniques for this being well known to one of ordinary skill in the art.

A weight percent of a component, unless specifically stated to the contrary, is based on the total weight of the formulation or composition in which the component is included.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. For example, an effective amount of neutralizer mousse composition will depend, in part, on the amount of hair being neutralized, the strength of the relaxer composition applied and the condition of the hair prior to application of the reducing agent. Thus, it is not possible herein to specify an exact "effective amount." However, an appropriate effective amount may be determined by one of ordinary skill in the art using only routine experimentation.

The present invention relates to compositions for neutralizing relaxed hair. Yet further, the present invention relates to a system for neutralizing relaxed hair. In one aspect, the invention pertains to neutralizer mousse compositions as discussed further herein. Still further, the present invention relates to processes for neutralizing reduced hair. Yet still further, the invention relates to relaxed hair that has been neutralized with the methods and compositions herein where the hair is less damaged than relaxed hair neutralized with prior art neutralizers that require substantial manipulation of the hair upon application of the neutralizer to the relaxed hair.

In a major aspect of the present invention, the neutralizing mousse composition comprises a foam, that is, a mousse formulation. Still further, the present invention comprises a system for neutralizing hair comprising a mousse concentrate and one or more propellants. Yet still further, the present invention comprises a kit for neutralizing hair comprising a relaxing agent and a neutralizer mousse composition. Still further, the kit does not include a neutralizer shampoo composition.

The pH of the neutralizer mousse compositions of the present invention is from about pH 3.5 to about pH 8.0, or from about pH 4.5 to about pH 7.0. Still further, the pH of the neutralizer mousse compositions of the present invention can be about 3.0, 3.5, 4.0, 4.5, 5.0, 5.5, 6.0, 6.5, 7.0 or 7.5, where any value can form an upper or a lower endpoint, as appropriate.

The pH of the neutralizer mousse compositions is conferred by the presence of acid in the compositions. The acid materials that can be used to provide an acidic pH to the neutralizer compositions comprises one or more acids from the following classes: (1) organic acids—examples include, but are not limited to, citric acid, lactic acid, glutamic acid, succinic acid, EDTA acid; (2) inorganic acids—examples include, but are not limited to, hydrochloric acid, and phosphoric acid; and (3) chemical reagents capable of functioning as proton donors which by virtue of this property form acidic solutions in water.

The neutralizer mousse compositions of the present invention may optionally comprise appropriate buffering agents for the particular acids used in the compositions. Such buffering agents would be known to one of ordinary skill in the art and accordingly are not discussed in detail herein.

In one aspect, the neutralizer mousse compositions of the present invention can comprise any propellant suitable for use to provide a mousse. In a further aspect, the neutralizer mousse compositions can comprise a single propellant. In still further aspects, the neutralizer mousse compositions can comprise a mixture of two or more propellants.

In particular, the neutralizer mousse compositions of the present invention will include a propellant that serves to expel a mousse concentrate from a container, and helps form the foam character that is understood to be present in mousse compositions. The propellant used in the neutralizer mousse compositions of the present invention can be any liquefiable gas conventionally used for aerosol containers. Examples of suitable propellants include dimethyl ether and hydrocarbon propellants such as propane, n-butane and isobutane. Water insoluble propellants, especially hydrocarbons, may be used because they generally form emulsion droplets on agitation and create suitable mousse foam densities.

In one aspect, the propellant in the neutralizer mousse compositions of the present invention can comprise a compressed gas. Examples of compressed gases are nitrogen, carbon dioxide, etc., which remain as gases in the container. If the gas is soluble in the liquid neutralizer formulation, the compressed gas can be partially solubilized in the liquid formulation. As known to one of ordinary skill in the art, the pressure that results from such a product can be controlled by the amount of propellant that is solubilized in the liquid concentrate and what is left in the head space.

In a further aspect, the neutralizer mousse compositions of the present invention can comprise a liquefied propellant. They are so-called because they are gases under normal temperature and pressure but become liquids under higher atmospheric pressure. As would be recognized by one of ordinary skill in the art, liquefied propellants may be advantageous in the mousse compositions because they generally maintain a constant pressure throughout the useful life of the mousse composition by converting from a liquid state to a gaseous state as the can is depleted. This provides the user with a product that does not vary too much in its properties over the dispensing life of the product. Suitable liquefied propellants are hydrocarbons, hydrofluorocarbons and dimethyl ether. Hydrocarbons used in the personal care industry can be mixtures of isobutane, n-butane and propane. The liquefied propellants can be blended to give the desired pressure. For example, hydrocarbon A-46 is a mixture of about 15.1% by weight of propane and about 84.9% by weight of isobutane blended to give about 46 psi pressure at about 70° F. If lower pressures are desired, then the propellants can be used as is. For example, n-butane has a pressure of about 17 psi at about 70° F. and isobutane has a pressure of about 31 psi at about 70° F. which can be used without blending.

Hydrofluorocarbons may also be used in the neutralizer mousse compositions present invention. One useful hydrofluorocarbon is Dymel 152A manufactured by Dupont, (Wilmington, Del.). Dymel 152A has a pressure of about 62 psi at about 70° F. which can make it desirable for a number of mousse formulations, including the neutralizer mousse compositions of the present invention. Dymel 152A is also denser than hydrocarbons which can be an advantage when filling cans to a desired weight.

In a further aspect, the neutralizer mousse compositions of the present invention can comprise $CO_2$ as a propellant. The $CO_2$ can be used alone or in combination with another propellant disclosed herein. It has been surprisingly found that mousse compositions comprising $CO_2$ as a propellant provide superior neutralization of hair neutralized in accordance with the methods herein. Such neutralization is at least equal to or, in some cases, superior to the neutralization seen with traditional "shampoo-type" neutralizers.

Further, it has been surprisingly found that if necessary, the foam quality of the neutralizer mousse compositions having $CO_2$ as a propellant can be improved when the mousse comprises a secondary propellant, such as the hydrocarbon, ether or halocarbon propellant materials discussed elsewhere herein.

In the formulation of the neutralizer mousse compositions of the present invention, the choice and amount of propellant will be significant in determining the amount and type of foam produced. One of ordinary skill in the art would readily recognize the formulation considerations needed to obtain foams of the desired consistency. As such, the details of these formulations are not discussed in detail herein.

Amounts of propellant in the neutralizer mousse compositions of the present invention may range from about 1 to about 40% by weight of the formulation, or from about 2 to about 15% by weight, or from about 3 and about 14% by weight based on the total weight neutralizer mousse concentrate and propellant combination in the container.

In manufacturing, the liquid concentrate is generally first filled into a container which is sealed with a valve cup, followed by introduction of the propellant via pressure filling. It is also possible to do "under the cup filling" where the propellant is filled and the valve cup sealed in one step.

When the propellant is a gas, as opposed to a liquid, the amount of propellant included in the container is generally measured in pounds per square inch ("psi"). In accordance with the present invention, the amount of gaseous propellant included in the neutralizer mousse compositions can be from about 25, 50, 100, 150, 200, 250 or 300 psi, where any value can be used as an upper or a lower endpoint as appropriate and which value is limited only by the mechanical strength of the container and valving used on the dispenser.

In some aspects, a propellant suitable for use herein may have a vapor pressure that should be reduced to improve the propellant's properties for use in a mousse composition. If a propellant such as dimethyl ether includes a vapor pressure suppressant (e.g. trichloroethane or dichloromethane), for weight percentage calculations of the amount of propellant included in the neutralizer mousse composition, the amount of suppressant is included as part of the propellant.

The method of preparing neutralizer mousse compositions of the present invention is in accordance with procedures known to one of ordinary skill in the art. In such an aspect, the neutralizer mousse composition ingredients (not including the propellant) are charged into a suitable pressurizable container which is sealed and then charged with the propellant according to known methods.

Depending on the type of properties desired in the final product, the mousse can comprise one or more surfactants in varying amounts. In one aspect, a low foaming composition can be provided using a low amount of surfactant. Still further, a higher amount of surfactant can be used to provide a higher foaming mousse. Yet still further, the propellant system can be varied to affect the final properties of the dispensed foam as discussed in more detail herein.

The neutralizer mousse compositions of the present invention will typically include one or more surfactants as described above in a total amount ranging from about 0.1% to 20%, or from about 0.1% to 15% by weight based on total weight of the neutralizer mousse compositions. Still further, the amount of surfactant may be from about 0.1, 0.5, 1, 2, 3, 4, 5, 6, 7, 8, 9, 10, 12, 15, 17 or 20% by weight, where any value can form an upper or a lower endpoint as appropriate.

A wide range of surfactants generally suitable for use in hair care formulations at acidic pH's can be used in the neutralizer mousse compositions of the invention. In various aspects, nonionic, cationic, anionic, amphoteric or zwitterionic surfactants can be used either alone, or in combination, in the compositions of the present invention. Still further, the surfactant in the neutralizer mousse compositions can comprise a mixture of one or more nonionic surfactants and one or more amphoteric or zwitterionic surfactants.

Examples of nonionic surfactants that may be used in the neutralizer mousse compositions of the present invention include, but are not limited to: condensation products of aliphatic ($C_8$-$C_{18}$) primary or secondary linear or branched chain alcohols or phenols with alkylene oxides, usually ethylene oxide and generally having from about 3 to 30 ethylene oxide groups. Other suitable nonionics include esters of sorbitol, esters of sorbitan anhydrides, esters of propylene glycol, fatty acid esters of polyethylene glycol, fatty acid esters of polypropylene glycol, ethoxylated esters and polyoxyethylene fatty ether phosphates. Examples of anionic surfactants are the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to about 10 ethylene oxide or propylene oxide units per molecule, and preferably contain about 2 to 3 ethylene oxide units per molecule.

Examples of cationic surfactants that may be used in the neutralizer mousse compositions of the present invention include, but are not limited to: cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, (and the corresponding hydroxides thereof), and those materials having the CTFA designations Quaternium-5, Quaternium-31 and Quaternium-18.

Examples amphoteric and zwitterionic surfactants that may be used in the neutralizer mousse compositions of the present invention include, but are not limited to: amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from about 8 to 19 carbon atoms.

Particularly suitable surfactants for use in the neutralizer mousse compositions of the present invention are surfactants that will exhibit satisfactory foaming at the acidic or near acidic pH's exhibited by the neutralizer mousse compositions of the present invention. Examples of surfactants suitable for use in the neutralizer mousse compositions of the present invention include but are not limited to salts of lauryl sulfate or lauryl ether sulfates including but not limited to the sodium, ammonium and triethanolamine salts of these surfactants, salts of sulfosuccinates for example sodium and disodium salts, betaine surfactants such as cocamidopropyl betaine, lauramidopropyl betaine, and sulfamidobetaine, propionates for example disodium cocoamphodipropionate; amphoacetates for example disodium cocoamphodiacetate, amine oxides for example cocamidopropyl amine oxide, carboxylates such as trideceth-7 carboxylic acid, sarcosinates such as sodium lauroyl sarcosinate, and foaming protein derivatives such as TEA-cocoyl hydrolyzed protein and TEA-lauroyl hydrolyzed collagen. It should be understood by one of skill in the art that the choice of surfactant or blend of surfactants for use in the present invention is limited only by considerations of the desired foaming properties, compatability with other mousse ingredients and long-term stability of the surfactant or surfactants at neutral or acid pH. Guidelines for surfactant use are available in the literature in such references as McCutcheon's Emulsifiers and Detergents and the actual suitability for use under the conditions of the present invention by any single surfactant or blend of surfactants can be determined by one of ordinary skill in the art without undue experimentation.

The neutralizer mousse compositions of the present invention can include one or more conditioning agents. In one aspect, the conditioning agent is of the type that would be suitable for application from an acidic pH. Still further, the conditioning agent can comprise a cationic polymeric conditioning agent such as, but not limited to, Polyquaternium-10, Polyquaternium-6, Polyquaternium-7, Polyquaternium-47, cationic guar and other water-soluble or dispersible polymeric conditioning agents.

Still further, the polymeric conditioning agent can comprise a non-ionic conditioning agent that is substantive to hair by virtue of its molecular weight, as opposed to electrostatic attraction. Such materials are well-known to one of ordinary skill in the hair care formulation art and will not be discussed in detail herein. One particularly suitable conditioning agent is AMAZE®, a corn starch-based conditioning agent available from National Starch and Chemical (Bridgewater, N.J.).

The neutralizer mousse compositions of the present invention are dispensed from the container as foams. In a significant aspect of the present invention, the neutralizer mousse compositions of the present invention are applied to hair that has been treated with relaxing agent, rinsed of the relaxer composition, but not yet neutralized. As set forth above, such hair is referred to herein as "relaxed hair."

As noted above, the neutralizer mousse compositions of the present invention have been found to provide effective neutralization when applied to relaxed hair. Surprisingly, it has been found that the neutralizing mousse compositions disclosed herein work as effectively and, in some instances, better than commercial shampoo-in neutralizers on relaxed hair. This effect was seen regardless of the propellant type used to provide the foam. Those skilled in the art can readily appreciate the fundamental problems one would expect from the use of foaming compositions for neutralizing relaxed hair.

Without being bound by theory, it is believed by the inventors herein that the formation of bubbles or lather actually ties up thin layers of the liquid neutralizing composition in the walls of the bubbles themselves. Because the acidic neutralizing compound or compounds is solubized in the same liquid tied up in the wall of each bubble, the formation of bubbles or lather is believed to have the effect of preventing the neutralizing compound from contacting the hair in all but the smallest of surface areas. Accordingly, the neutralizing agent cannot penetrate into the hair fiber to complete the task of neutralizing excess alkalinity until the bubbles have begun to burst and the liquid is freed to diffuse into the fiber. Surprisingly, it has been determined herein that the mousse-type neutralizers of the present invention are extremely effective neutralizers despite the presence of the large quantity of lather. This result was unexpected by the inventors herein.

Further, without kneading or massaging of a shampoo neutralizer into the hair, relaxed hair has been found to be significantly less likely to break due to the reduction of force applied to the hair when it is in its weakened, relaxed form. As such, it has also been surprisingly found that relaxed hair neutralized with the neutralizer mousse compositions of the present invention exhibits significantly less breakage than hair neutralized with the usually-applied shampoo neutralizer formulations.

Accordingly, one aspect of the present invention relates to a process for neutralizing relaxed hair.

In one aspect of the process for neutralizing relaxed hair, the neutralizer mousse compositions of the present invention are applied to a head of relaxed, but not yet neutralized hair. Upon application of an amount sufficient to coat the hair, the neutralizer mousse composition remains in contact with the hair for about 30 seconds, about 1 minute, about 2 minutes, about 3 minutes, about 4 minutes, about 5 minutes, about 6 minutes, about 7 minutes, about 8 minutes, about 9 minutes, or about 10 minutes or about 20 minutes. Still further, there are about 1, 2, 3, 4 or 5 separate applications of the neutralizer mousse compositions. In these aspects, the hair may or may not be rinsed prior to the further application of the neutralizer mousse compositions.

In one aspect, the neutralizer mousse composition is not massaged into the hair upon application thereof. Still further, upon application of the neutralizer mousse compositions to the hair, the mousse is lightly stroked in a downward motion directed toward the ends of the hair, as opposed to manipulating the hair in a massaging or kneading motion. This motion is similar or, in some aspects, identical to the "smoothing" action used to ensure suitable incorporation of the relaxing agent into the hair during the relaxing process. Still further, suitable incorporation of the neutralizer mousse composition into relaxed hair is accomplished with substantially no physical manipulation of the relaxed hair.

The reduction in damage seen with the methods of the present invention is manifested in there being fewer broken hair fibers in hair that has been neutralized with the neutralizer mousse compositions of the present invention, where the number of broken hair fibers is measured in comparison to the number of broken hair fibers resulting from hair that has been relaxed and then neutralized with prior art shampoo neutralizer compositions.

In accordance with this aspect, relaxed hair neutralized with the neutralizer mousse compositions of the present invention exhibits at least about 10% less breakage, or at least about 15% less breakage, or at least about 20% less breakage or at least about 25% less breakage, when compared to relaxed hair treated with shampoo-type neutralizers. Still further, hair relaxed with a no-lye relaxing agent followed by neutralization with the neutralizer mousse compositions of the present invention exhibits significantly less breakage than hair relaxed with a no-lye relaxing agent followed by neutralization with a shampoo-type neutralizer. Still further, hair relaxed with a lye relaxing agent followed by neutralization with the neutralizer mousse compositions of the present invention exhibits significantly less breakage than hair relaxed with a lye relaxing agent followed by neutralization with a shampoo-type neutralizer.

In accordance with one aspect of the present invention, the amount of alkalinity in the hair is determined by the internal pH of the hair. The internal pH is determined by soaking hair that has been relaxed and neutralized in distilled water and measuring the pH of the water after a time period. The pH of the water after soaking of the hair for the specified time is the internal pH of the relaxed and neutralized hair.

It has been found that the internal pH of the hair after application of the neutralizer mousse compositions is at or below the internal pH of hair that has been treated with prior art shampoo-type neutralizer compositions. This is surprising because, as noted above, it was thought that in order to obtain sufficient neutralization of relaxed hair it was necessary to apply substantial physical manipulation to relaxed hair and to apply a shampoo-type neutralizer composition. These compositions contain a pH indicator whereby the shampoo changed color when a certain pH was obtained. In order to obtain a full color change, it was required that the shampoo-type neutralizer be massaged or kneaded into the hair several times. As noted above, the application of such a force to the hair results in significant damage to the hair because relaxed hair is extremely breakable prior to neutralization.

In one aspect, the neutralizer mousse composition remains on the hair for a time period sufficient to provide a pH of about 11.0 or below when approximately 1 gram of relaxed hair is soaked in about 100 grams of distilled water for about 5 minutes where the water pH is measured. Still further, the neutralizer mousse composition remains on the hair for a period of time sufficient to provide a pH of about 10.0 or about 11.0 or below when approximately 1 gram of relaxed hair is soaked in about 100 grams of distilled water for about 10 minutes where water pH is measured. Still further, the neutralizer mousse composition remains on the hair for a period of time sufficient to provide a pH of 11.0 or 10.0 or below when approximately 1 gram of relaxed hair is soaked in about 100 grams of distilled water for about 20 minutes where the water pH is measured.

As would be understood by one of ordinary skill in the art, the pH of water in which the relaxed and neutralized hair has been soaked is directly related to the amount of alkaline material that remains in the hair after neutralization. A low initial water pH i.e., after about 5 minutes of soak or less, is an indicator that the relaxed hair has been significantly neutralized after application of the neutralizer mousse compositions or shampoo-type neutralizer. Further, the pH of the water soaks at longer times i.e., about 10, 15 or 20 minutes are indicative of the residual amount of alkalinity contained within the relaxed and neutralized hair fibers. As illustrated by the Examples presented below, the water soak pH's of relaxed hair treated with the neutralizer mousse compositions of the present invention are equal to or less than the water soak pH's of relaxed hair treated with prior art shampoo-type neutralizer compositions at all water soak times measured. These pH results demonstrate that the neutralizer mousse compositions of the present invention provide excellent neutralization of relaxed hair.

In one aspect, an effective amount of neutralizer mousse composition is applied to relaxed, but not yet neutralized, hair. An effective amount of neutralizer mousse composition is the amount of neutralizer that results in a pH after a 5 minute water soak of about pH 10.5 or less or about pH 10.0 or less. The conditions for the water soak are as discussed above.

While the neutralizer mousse compositions can remain in the relaxed hair for a suitable time so as to provide substantial neutralization of the relaxed hair, as would be recognized by one of ordinary skill in the art, in some aspects it may be useful to include a pH indicator in the neutralizer mousse compositions of the present invention. Such indicators allow the operator or consumer to obtain a sense of security that the neutralization process is complete by a signaling of a pH change when a suitable amount of alkalinity is eliminated from the hair. Suitable pH indicator materials are well-known in the art and are not discussed in detail herein. Once such suitable material is phenolsulfonphthalein also known as "Phenol Red." Techniques for incorporating this material into a neutralizer product are well-known to one of ordinary skill in the art and, as such, are not discussed in detail herein.

After the neutralizer mousse composition has remained on the hair for a sufficient time as defined herein or when the pH indicator signals a suitable pH change, the neutralizer mousse compositions can be rinsed from the hair. Still further, the neutralizer mousse compositions can be left in the hair. Yet still further, the hair can be styled as usual after application of the neutralizer mousse compositions of the present invention. In a further aspect, the hair can be shampooed after one or more applications of the neutralizer mousse composition of the present invention.

In one aspect, the mousse neutralizer compositions of the present invention comprise an aqueous solution of water-soluble acidic materials capable of neutralizing alkalinity on or in relaxed hair and an effective amount of a material that is suitable to provide a foam. However, one reasonably skilled in the art would recognize that the present invention can be modified to enhance the qualities of the foam obtained, the condition of the hair, and the organoleptic qualities of both the foam and the relaxed hair.

Examples of other ingredients which may be present in the neutralizer mousse compositions of the present invention include, but are not limited to: (1) viscosity adjusters and foam stabilizers like amine oxides, alkanolamides, and polymeric thickening agents; (2) pH adjusting agents and buffering agents designed to prevent age-induced changes in formula characteristics or surfactant degradation; and (3) specialty additives which impart improved organoleptic properties to the foam and/or the treated hair (examples include conditioning agents, proteins, re-fatting agents, anti-irritants, etc.) Such materials and the incorporation thereof into hair care products are well-known to one or ordinary skill in the art and, as such, is not discussed in detail herein.

EXPERIMENTAL

The following Examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° F. or is at room temperature, and pressure is at or near atmospheric.

Each of the neutralizer mousse compositions evaluated in the Examples below were prepared using mousse concentrates MC1 or MC2 as indicated in the respective examples. The mousse dispensers were charged with the specified propellant using conventional methods.

| MOUSSE CONCENTRATE FORMULATIONS | | |
|---|---|---|
| Ingredient | Amount (g) | Source |
| A. Mousse Concentrate 1 ("MC1") | | |
| Water | q.s. to 100 | Deionized tap water |
| DMDM hydantoin | 0.50 | Lonza, Inc. (Fair Lawn, NJ) |
| Propylene glycol | 1.00 | Jeen Chemical (Fairfield, NJ) |
| Glutamic acid | 0.60 | Fisher Scientific (Hampton, NH) |
| Monosodium glutamate | 0.60 | Fisher Scientific (Hampton, NH) |
| Gafquat 755 N | 6.00 | ISP Corp. (Wayne, NJ) |
| Monaquat TG | 1.00 | Uniqema (New Castle, DE) |
| Tween 20 | 1.00 | ICI Surfactants (Wilmington, DE) |
| Silwax WSL | 2.00 | Siltech, Inc. (Toronto, CA) |
| Phenol red | 0.01 | Pylam Dye (Tempe, AZ) |
| Fragrance | 0.40 | Intarome Fragrance (Norwood, NJ) |
| B. Mousse Concentrate 2 ("MC 2") | | |
| Water | q.s. to 100 | Deionized tap water |
| Methyl paraben | 0.20 | Jeen Chemical |
| Propyl paraben | 0.20 | Jeen Chemical |
| Polymer JR30M | 0.40 | Amerchol Corp. (Dow Chemical, Freeport, TX) |
| Propylene glycol | 1.00 | Jeen Chemical |
| AMAZE | 1.0 | National Starch and Chemical |
| Phenol Red | 0.01 | Pylam |
| Triethanolamine, 98% | 0.56 | Fisher Scientific |
| Citric acid | 0.41 | Fisher Scientific |
| Cocamidopropyl betaine (30%) | 13.50 | McIntyre Group (University Park, IL) |
| Disodium laureth sulfosuccinate | 5.00 | McIntyre Group |
| Polysorbate-20 | 1.00 | ICI Surfactants |
| DMDM Hydantoin | 0.40 | Lonza, Inc. |
| Fragrance | 0.25 | Intarome Fragrance |

Example 1

Procedure for Relaxing and Neutralizing Hair

Materials: DeMeo African Kinky Hair (DeMeo Brothers, Ltd.; New York)
Alkaline Hair Straightening Composition
Applicator Brush and/or Smoothing Comb
Rinse Water
Neutralizing Compositions
pH meter standardized to pH 7.0 and pH 10.0
Distilled Water
150-mL beakers
Tresses of DeMeo African Kinky hair were bound at the proximal end. Each tress contained approximately one gram of hair For the Comparative Examples and the relaxed hair treated with the neutralizer mousse compositions of the present invention, an alkaline guanidine-based relaxer composition was applied to hair. Unless otherwise specified, all examples were treated with a relaxer composition comprising a 1:1 mixture of 8% by weight $Ca(OH)_2$ cream base and a 12% by weight guanidine carbonate cream base. After thorough mixing of the compositions, an applicator brush was used to apply the relaxer composition to African Kinky hair and timing was begun. The relaxer composition remained on the hair for 20 minutes. During that time, the applicator brush was used to smooth the hair twice (once 5-min after initial application and again 15-min after the initial application). After 20 min, excess relaxer was rinsed from the tress using tap water. The tress was very lightly blotted with fingertips to remove excess water. The tress was then ready for immediate treatment with neutralizing composition(s).

For the Comparative Examples, the identified shampoo-type neutralizer compositions were applied to the hair and allowed to remain in contact with the hair as directed by the manufacturer. In the case of commercial shampoo neutralizer products, the tresses were repeatedly shampooed until the lather formed during shampooing no longer turned pink.

In the case of the neutralizing mousse compositions of the present invention, unless otherwise specified, mousse was sprayed onto hair in an amount sufficient to saturate the hair and allowed to remain on the hair for 1 minute. The hair was not massaged or kneaded while the neutralizer mousse composition was on the hair. The pH of all neutralizer mousse compositions was between pH 4.0 and 6.0.

When noted, the neutralizer mousse composition was applied in multiple applications. All tresses were rinsed with water after each application of neutralizing composition. After the final application of neutralizing composition, each tress was rinsed with distilled water and blotted.

Example 2

Determination of the Internal pH of Relaxed and Neutralized Hair

To determine the internal pH of the hair, relaxed and neutralized tresses were placed in a beaker containing 100 grams of distilled water and a standardized pH electrod. The pH of the distilled water soak was recorded at 5 minute intervals for 5 to 20 min.

Example 3 pH Results for Neutralization of Hair With Neutralizer Mousse Compositions Prepared From MC1

Neutralizer mousse compositions were prepared from MC1 as set out above. Mousse formulations conforming to various neutralizer mousse compositions of the present invention were prepared using conventional filling techniques with the propellants as specified.

Tresses were relaxed and neutralized with the neutralizer mousse compositions of the present invention according to the procedure in Example 1. The pH results are as follows:

| | | pH of water soak after, | | | |
|---|---|---|---|---|---|
| Sample | Propellant | 5 min | 10 min | 15 min | 20 min |
| 010-1 | A-70 at 6.0 wt % | 10.50 | 10.77 | 10.80 | 10.88 |
| 010-2 | A-46 at 6.0 wt % | 10.48 | 10.73 | 10.84 | 11.01 |
| 010-3 | 134a at 6.0 wt % | 9.75 | 10.17 | 10.26 | 10.30 |
| 010-4 | $CO_2$ at 5.0 wt % | 8.40 | 8.76 | 9.20 | 9.21 |

The above results demonstrate that neutralizer mousse compositions of the present invention provide significant neutralization to relaxed hair.

Example 4

Comparative Examples

Determination of pH of Hair Relaxed and Neutralized With Commercial Relaxer Formulations A number of commercially available neutralizer products typically recommended for use after a relaxer treatment were tested on hair treated with the guanidine-type relaxer specified above in Example 1. The neutralizer compositions were as supplied in commercially available hair relaxer products. Each product was evaluated on two occasions so that the reproducibility of the results was clearly demonstrated.

| Product/Mfr | 5 min pH | 10 min pH | 15 min pH | 20 min pH |
|---|---|---|---|---|
| Optimum Care (Soft Sheen Carson) | 9.69 | 9.85 | 9.98 | n/d |
| Optimum Care (Soft Sheen Carson) | 9.56 | 9.88 | 9.99 | 10.15 |
| Synthesis III (Soft Sheen Carson) | 9.66 | 9.88 | 9.96 | 10.05 |
| Synthesis III (Soft Sheen Carson) | 9.62 | 9.9 | 9.98 | 10.19 |
| Gentle Treatment (Johnson Products) | 9.78 | 10.19 | 10.41 | n/d |
| Gentle Treatment (Johnson Products) | 9.32 | 10.28 | 10.48 | 10.57 |
| Dark & Lovely (Soft Sheen Carson) | 9.84 | 10.35 | 10.46 | n/d |
| Soft-n-Beautiful (Pro-Line Corp) | 9.97 | 10.17 | 10.28 | n/d |
| IsoPlus (JM Products) | 9.82 | 9.99 | 10.56 | 10.91 |
| Elasta QP (Elasta Products) | 9.83 | 10.23 | 10.38 | 10.55 |
| Clariol Textures (Clairol) | 10.44 | 10.52 | 10.62 | 10.71 |

"n/d" means data for this time point were not obtained.

Example 4

Effect of Extended Neutralization Times and Multiple Treatments on pH of Relaxed and Neutralized Hair

| | | | pH of water soak after, | | |
|---|---|---|---|---|---|
| Sample | | | 5 min | 10 min | 15 min |
| EXTENDED TREATMENT TIMES NEUTRALIZER MOUSSE COMPOSITIONS WITH MC2 | | | | | |
| 108-1 | $CO_2$ at 50 psi | 5 MIN | 9.7 | 10.2 | 10.31 |
| 108-2 | $CO_2$ at 100 psi | 5 MIN | 10.31 | 10.61 | 10.73 |
| 108-3 | $CO_2$ at 150 psi | 5 MIN | 9.65 | 10.73 | 10.81 |
| MULTIPLE TREATMENTS NEUTRALIZER MOUSSE COMPOSITIONS WITH MC2 | | | | | |
| 118-1 | $CO_2$ Saturation & Purge | First | 9.59 | 10.27 | 10.29 |
| 118-2 | $CO_2$ Saturation & Purge | Second | 9.31 | 9.68 | 9.7 |
| 118-3 | $CO_2$ Saturation & Purge | Third | 8.86 | 9.17 | 9.54 |
| 119-2 | $CO_2$ Saturation & Purge | First | 9.91 | 10.45 | 10.48 |
| 119-3 | $CO_2$ Saturation & Purge | Second | 9.9 | 10.14 | 10.21 |
| 119-4 | $CO_2$ Saturation & Purge | Third | 8.81 | 9.1 | 9.34 |

This example shows that extended treatment times and multiple applications of the neutralizer mousse compositions of the present invention can lower the internal pH of the hair.

Example 5

Effect of Propellant Type and Amount on Neutralization Effectiveness

| Sample | NEUTRALIZER MOUSSE COMPOSITIONS TYPE | 5 min | 10 min | 15 min |
|---|---|---|---|---|
| | NEUTRALIZER MOUSSE COMPOSITIONS prepared with MC1 | | | |
| 008-1 | MC1; A-70 propellant at 6.0 wt % | 10.5 | 10.77 | 10.8 |
| 008-2 | MC1; A-46 propellant at 6.0 wt % | 10.48 | 10.73 | 10.84 |
| 008-3 | MC1; 134a propellant at 6.0 wt % | 9.75 | 10.17 | 10.26 |
| 008-4 | MC1; $CO_2$ propellant at 5.0 wt % | 8.4 | 8.76 | 9.2 |
| 108-1 | MC2; with $CO_2$ at 50 psi | 10.44 | 10.82 | 10.81 |
| 108-2 | MC2; with $CO_2$ at 100 psi | 9.61 | 10.46 | 10.64 |
| 108-3 | MC2; with $CO_2$ at 150 psi | 10.41 | 10.82 | 10.96 |
| 129-1 | MC2; $CO_2$ saturation and purge | 9.61 | 9.66 | 9.69 |
| 129-1 | MC2; $CO_2$ saturation and purge | 9.74 | 9.95 | 9.97 |
| 129-1 | MC2; $CO_2$ saturation and purge | 9.41 | 9.73 | 9.88 |

In this example, hair was relaxed for 20 min with a mixture of 8% $Ca(OH)_2$ cream base (60 grams) and 12% guanidine carbonate cream base (40 grams). After rinsing the relaxer composition from the hair, each tress was coated with mousse. The mousse was allowed to remain on the hair for 1 min. After 1 min the tress was thoroughly rinsed with tap water and blotted prior to further testing.

This example shows that various propellant types may be used in the neutralizer mousse compositions of the present invention to provide effective neutralization.

Example 6

Effect of Propellant on Neutralization Effectiveness

| | | pH of water soak after | | | |
|---|---|---|---|---|---|
| Sample | Propellant | 5 min | 10 min | 15 min | 20 min |
| 127-1 | $CO_2$ | 9.4 | 10.33 | 10.49 | 10.46 |
| 128-1 | 5 wt % $CO_2$, 1X | 8.81 | 9.83 | 9.87 | 9.92 |
| 129-1 | AB-46 | 10.65 | 10.67 | 10.7 | 10.82 |
| 130-1 | 152A | 10.3 | 10.46 | 10.67 | 10.69 |
| 139-3 | 5 wt % P-134a, 1X | 10.31 | 10.58 | 10.89 | 10.91 |
| 140-1 | 5 wt % P134a/$CO_2$, 1X | 10.33 | 10.55 | 10.6 | 10.63 |
| 127-2 | $CO_2$ | 8.32 | 9.18 | 9.2 | 9.23 |
| 128-2 | 5 wt % $CO_2$, 2X | 8.29 | 8.73 | 9.09 | 9.19 |
| 129-2 | AB-46 | 9.09 | 10.11 | 10.14 | 10.16 |
| 130-2 | 152A | 9.43 | 9.99 | 10.4 | 10.44 |
| 139-4 | 5 wt % P-134a, 2X | 10.28 | 10.54 | 10.68 | 10.77 |
| 140-2 | 5 wt % P134a/$CO_2$, 2X | 9.64 | 9.99 | 10.17 | 10.38 |
| 127-3 | $CO_2$ | 8.51 | 9.29 | 9.47 | 9.5 |
| 128-3 | 5 wt % $CO_2$, 3X | 8.23 | 8.53 | 8.8 | 8.78 |
| 129-3 | AB-46 | 8.65 | 9.1 | 9.47 | 9.51 |
| 130-3 | 152A | 8.8 | 10.27 | 10.32 | 10.34 |
| 139-5 | 5 wt % P-134a, 3X | 9.88 | 10.31 | 10.52 | 10.52 |
| 140-3 | 5 wt % P134a/$CO_2$, 3X | 8.99 | 9.64 | 9.85 | 9.92 |

This example shows that different propellant types can provide effective neutralization to relaxed hair. 1×, 2× and 3× indicates number of times the neutralizer mousse composition was applied to the neutralized hair.

HFC 134a is supplied by DuPont Corporation (Wilmington, Del.). A-46 Propellant is supplied by Aeropres Corporation (Shreveport, La.). AB-46 is supplied by Diversified CPC Intl. (Chinnanon, Ill.). P-134a is supplied by Technical Propellents Inc. (Ponca City, Okla.).

Example 7

Effect of Mixed Propellant System on Neutralization Effectiveness

| | | pH of deionized water soak at | | | |
|---|---|---|---|---|---|
| Sample | Propellant | 5 min | 10 min | 15 min | 20 min |
| | NEUTRALIZER MOUSSE COMPOSITIONS MADE WITH MC2 | | | | |
| 157-1 | 2% A-46 & 100 psi $CO_2$ | 9.61 | 9.8 | 10.6 | 10.61 |
| 158-1 | 1% A-46 & 100 psi $CO_2$ | 9.26 | 9.82 | 10.38 | 10.39 |
| 157-2 | 2% A-46 & 100 psi $CO_2$ | 8.83 | 9.23 | 9.24 | 9.23 |
| 158-3 | 1% A-46 & 100 psi $CO_2$ | 8.83 | 9.21 | 9.3 | 9.3 |

Neutralization data are based on three 1-min applications of mousse to relaxed hair. This example shows that a mixed propellant system neutralizer mousse compositions provides excellent neutralization of relaxed hair. The hair was rinsed between applications.

Example 8

Neutralization Effectiveness of MC2 Dispensed From Spray-Type Mousse Containers

| | pH of water soak after, | | | |
|---|---|---|---|---|
| Sample | 5 min | 10 min | 15 min | 20 min |
| 164-1 | 10.27 | 10.35 | 10.64 | 10.66 |
| 164-2 | 9.46 | 9.83 | 10.09 | 10.12 |
| 164-3 | 9.15 | 9.7 | 9.88 | 9.99 |
| 164-4 | 9.77 | 10.39 | 10.64 | 10.7 |

(1) Samples were packaged in aerosol cans equipped with spray-type nozzles rather than mousse nozzles. P-134a was used to aerosolize the above samples and the last digit in the sample code represents the percentage of propellant.

The above data show that the neutralizer mousse compositions of the present invention effectively neutralize relaxed hair when dispensed from spray-type mousse containers.

Example 9

Neutralizer Effectiveness of MC2 Neutralizer Mousse Formulation Having Mixed $CO_2$-Butane Propellant System

| | pH of water soak after, | | | |
|---|---|---|---|---|
| Sample | 5 min | 10 min | 15 min | 20 min |
| 011-1 | 8.86 | 9.21 | 9.47 | 9.49 |
| 011-2 | 9.63 | 10.28 | 10.53 | 10.53 |

The neutralizer mousse compositions of this example had a propellant of 2.0% butane and carbon dioxide which was filled via impact gassing.

Example 10

Evaluation of Hair Breakage with Hair Relaxed with No-Lye Relaxers and Neutralized With Neutralizer Mousse Compositions and Competitive Shampoo Neutralizers

No-Lye Relaxer Products Used in Study
(type of neutralizer supplied with product)
A. Dark & Lovely - L'Oreal S.A., New York, NY - (shampoo neutralizer)
B. Optimum - Soft Sheen, Chicago, IL - (shampoo neutralizer)
C. Soft & Beautiful - Alberto-Culver, Melrose Park, IL - (shampoo neutralizer)
D. Precise - Wella Group, Woodland Hills, CA - (shampoo neutralizer)
E. P-Profectiv - Strength of Nature, Savannah, GA - (neutralizer mousse)
The neutralizer mousse in the Profectiv product has the following formulation (sources as in Example 1):

| INGREDIENT | WT % |
|---|---|
| Part A | |
| Water | q.s. to 100 |
| Preservative | 1.00 |
| Polymer JR30M | 0.40 |
| AMAZE | 1.00 |
| Part B-Premix | |
| Water | 1.00 |
| Triethanolamine, 88% | 0.56 |
| Part C-Premix | |
| Water | 1.00 |
| Phenol Red (Indicator) | 0.01 |
| Part D-Premix | |
| Water | 1.00 |
| Citric Acid, anhydrous | 0.41 |
| Part E | |
| Cocamidopropylbetaine, 30% | 6.75 |
| Mackinate EL | 2.50 |
| Part F-Premix | |
| Polysorbate 20 | 1.00 |
| Fragrance and natural extracts | 0.40 |

The premix ingredients were mixed together to form a mousse concentrate. The mousse concentrate was charged into a mousse dispenser along with a mixture of carbon dioxide at 100 psi and A-46 propellant at 2% by weight.

The salon evaluator parted a head of hair into two sections down the middle. The left side of the head was defined and then one of either of the no-lye relaxers denoted A, B, C or D was applied to one side of the half head. Each other half head had a single no-lye relaxer applied to the head (Profectiv, Strength of Nature LLC, Savannah, Ga.). In the relaxer application and neutralizing process, care was taken to keep products separate on each side of the head. After completion of the relaxing and neutralizing steps, the salon evaluator took care to collect broken hair that had fallen out from each side of head. Broken hair from each side of the head was then placed in a marked container. After broken hair naturally dried inside the marked container, the evaluator counted broken hair from each half head side. The hair count is shown in Table 1.

TABLE 1

COMPARISON OF HAIR RELAXED WITH NO LYE RELAXERS AND TREATED WITH SHAMPOO-TYPE NEUTRALIZER AND NEUTRALIZER MOUSSE COMPOSITIONS

| Head Number | Type of relaxer per each half of head | Number of Broken Hairs: Neutralizer Mousse Composition | Number of Broken Hairs: Shampoo Neutralizers | % Decrease in Number of Broken Hairs with Neutralizer Mousse Composition |
|---|---|---|---|---|
| 1 | P/A | 39 | 58 | −33% |
| 2 | P/B | 55 | 75 | −27% |
| 3 | P/C | 35 | 47 | −26% |
| 4 | P/B | 60 | 75 | −20% |
| 5 | P/A | 204 | 316 | −35% |
| 6 | P/D | 55 | 70 | −21% |
| 7 | P/C | 40 | 65 | −38% |
| 8 | P/B | 62 | 87 | −29% |
| 9 | P/B | 107 | 130 | −18% |
| 10 | P/A | 67 | 100 | −33% |
| 11 | P/D | 100 | 147 | −32% |
| 12 | P/C | 66 | 79 | −16% |
| 13 | P/A | 125 | 155 | −19% |
| TOTAL | | 1015 | 1404 | −28% |

From the above data, which are presented in graphic form in FIG. 1, it is apparent that hair relaxed with no-lye relaxer that is neutralized using a neutralizer mousse composition of the present invention exhibits significantly less breakage than hair on the same head that has been relaxed with a no-lye relaxer and neutralized with a shampoo-type neutralizer product. Moreover, the evaluators consistently rated the neutralizer mousse composition treated hair as shinier and softer than hair treated with shampoo-type neutralizers. Further, the evaluators recognized that hair neutralized with the neutralizer mousse compositions of the present invention had increased tensile strength. These results demonstrate that the neutralizer mousse compositions of the present invention provide results that are superior to neutralization with competitive shampoo-type neutralizer compositions.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit invention. Other aspects of the invention will be apparent to those skilled in the art consideration of the specification and practice of the invention disclosed herein. It is intended that the specification and examples be considered as exemplary only, with a true and spirit of the invention being indicated by the following claims.

What is claimed is:

1. A method for neutralizing relaxed hair comprising:
   a) providing hair that has been treated with a relaxing agent;
   b) contacting the relaxed hair with one or more applications of a neutralizer mousse composition for from about 30 seconds to about 20 minutes, wherein the hair is not massaged or kneaded while the neutralizer mousse composition is in contact with the relaxed hair wherein after step b), the relaxed and neutralized hair exhibits at least 20% fewer broken hair fibers as compared to relaxed hair that has been neutralized with a shampoo neutralizer product; and
   c) rinsing the neutralizer mousse composition from the relaxed hair, thereby providing hair that has been relaxed and neutralized wherein the neutralizer mousse composition comprises: a) a mousse concentrate comprising water, an acid and a surfactant; and b) one or more propellants.

2. The method of claim 1, wherein the relaxing agent comprises a no-lye relaxing agent.

3. The method of claim 1 wherein step b) is repeated from about 1 to about 5 additional times.

4. The method of claim 1, wherein the neutralizer mousse composition remains in contact with the hair for from about 30 seconds to about 5 minutes.

5. The method of claim 1, wherein the relaxed and neutralized hair has an internal pH of from about 7.0 to about 11.0 after rinsing of the neutralizer mousse composition from the relaxed hair, wherein the internal pH is measured after soaking about 1 gram of hair in about 100 ml of distilled water for about 5 minutes.

6. The method of claim 1, wherein the relaxed and neutralized hair has an internal pH of from about 8.5 to about 10.5 after rinsing of the neutralizer mousse composition from the relaxed hair, wherein the internal pH is measured after soaking about 1 gram of hair in about 100 ml of distilled water for about 5 minutes.

7. The method of claim 1, wherein the one or more propellants comprises carbon dioxide.

8. The method of claim 1, wherein the one or more propellants comprise one or more of: a hydrocarbon, a hydroflurocarbon or dimethyl ether.

9. The method of claim 1, wherein the one or more propellants comprises a mixture of carbon dioxide and one or more of: a hydrocarbon, a hydroflurocarbon or dimethyl ether.

10. The method of claim 1, wherein the neutralizer mousse composition has a pH of from about 3.5 to about 8.

11. The method of claim 1, wherein the neutralizer mousse composition is applied from a container suitable for dispensing a foam.

12. The method of claim 1, wherein the one or more propellants comprises carbon dioxide, wherein the pressure of the $CO_2$ in the container is from about 50 to about 200 psi.

* * * * *